United States Patent [19]

Hutchinson et al.

[11] Patent Number: 4,748,181

[45] Date of Patent: May 31, 1988

[54] METHOD FOR TREATING HYPERTENSION WITH NICOTINE

[75] Inventors: Ronald R. Hutchinson; Grace S. Emley, both of Augusta, Mich.

[73] Assignee: Foundation for Behavioral Research, Augusta, Mich.

[21] Appl. No.: 734,764

[22] Filed: May 15, 1985

Related U.S. Application Data

[63] Continuation of Ser. No. 70,367, Aug. 28, 1979, abandoned.

[51] Int. Cl.⁴ ............................................. A61K 31/44
[52] U.S. Cl. .................................................... 514/343
[58] Field of Search ......................................... 514/343

[56] References Cited

U.S. PATENT DOCUMENTS

3,870,794  3/1975  Hutchinson .

OTHER PUBLICATIONS

Nicotine and Renal Hypertension in the Rat, D. G. Wenzel, A. Wattanapongsiri and D. Vedral, J. Pharmacology & Experimental Therapeutics, vol. 145, pp. 315-316 (1964).

Studies on Mode of Action of Monoamine Oxidase Inhibitors on the Experimental Hypertension of the Rat, Chika Nagata, pp. 11-20 (319-328) (1970).

Nicotine Effects in Spontaneously Hypertensive Rats, A. S. Weltman et al., Federation Proceedings 32(3) 806 Abs. (1973).

Influence of Chronic Nicotine Administration on Blood Pressure and Heart Norepinephrine Turnover, Thomas C. Westfall, European Journal of Pharmacology, vol. 10, pp. 19-24 (1970).

Effects of Chronic Administration of Nicotine on Storage and Synthesis of Noradrenaline in Rat Brain, B. Bhagat, Br. J. Pharmac. (1970), vol. 38, pp. 86-92.

Tobacco Smoke; Comparison of Chamber and Face Mask Exposure Systems in Guinea Pigs, R. E. Goldhamer, S. Carson and E. E. Vogin, Toxicology and Applied Pharmacology, vol. 14, p. 616 (1969).

Nickerson, Goodman & Gilman (eds.) The Pharm. Basis of Therapeu-Macmillan, NY 1965 pp. 727-731.

Merck Manual of Diag. & Therapy, Merck & Co. Rahway NJ 10th Ed. 1961 pp. 210-217.

Vander et al., Human Physiol., McGraw-Hill, NY, 1970 pp. 297-298.

Best & Taylor, The Physiol. Basis of Med. Practice, Williams & Wilkins, Baltimore, 5th Ed. 1950 pp. 162-166.

Porsius, Chem. Abs., vol. 87, 1977 Ab. No. 87:177791f.

Wenzel, Arch. Internat. de Pharmacody et Therap. vol. 193, 1971 pp. 23-36.

Henry et al., Amer. J. Epidemiology, vol. 90, 1969 pp. 171-200.

Iwaki et al., Nippon Yakurigaku Zasshi, vol. 63, 1967 pp. 472-486.

Porsius et al., Prog. Brain Res., vol. 47, 1977 pp. 131-135.

Goodman & Gilman (Eds) Pharm. Basis of Therap., 5th Ed. 1975 pp. 705-726.

Larson, Tobacco-Exptl. & Clinical Studies, Supplement II Williams & Wilkins, Pub. Balto. Sections 340-349.

Karvonen, The Lancet, I Mar. 1959 pp. 492-494.

Thomas Annals. Int. Med., vol. 53, Oct., 1960 pp. 697-718.

Porsius et al., Arzneim-Forsch./Drug Res., 28 (II), Sep. 1978 pp. 1628-1631.

Bisset et al., Br. J. Pharmac., vol. 54, 1975 pp. 463-474.

Harrison's Principles of Int. Med. 7th Ed. 1974, McGraw-Hill, N.Y. pp. 188-191, 1236-1246.

Tobacco-Experimental & Clinical Studies, Supp. III 1975, Williams & Wilkins, Balt., Sections 340-349.

(List continued on next page.)

*Primary Examiner*—Sam Rosen
*Attorney, Agent, or Firm*—Flynn, Thiel, Boutell & Tanis

[57] ABSTRACT

Hypertension is treated by chronic administration of nicotine or pharmaceutically acceptable salt of nicotine. More specifically, essential hypertension is treated in primates using effective dosages of nicotine.

5 Claims, 3 Drawing Sheets

OTHER PUBLICATIONS

Roth, JAMA, vol. 125, Jul. 15, 1944 pp. 761–767.
Wenzel et al., Arch. Intnat. de Pharm. et Therapie, vol. 187, No. 2, Oct. 1970 pp. 367–376.
Bremer et al.–Chem. Abst. vol. 55 (1961) p. 777a.
Iwaki et al., Chem. Abst. vol. 69 (1968) p. 66036x.
Greene, J. Chron. Dis. vol. 36, pp. 401–413.
Carruthers, Psychological Med., vol. 6, 1976 pp. 251–256.
Frankenhaeuser, Scand. J. Psychol. vol. 11, 1970 pp. 237–245.
Roth, Annals N.Y. Acd. Sci., vol. 90, Sep. 27, 1960 Atel, pp. 308–316.
Lucchesi, Clin. Pharmacol & Therap. vol. 8, No. 6, 1967 pp. 789–796.

METHOD FOR TREATING HYPERTENSION WITH NICOTINE

This application is a continuation, of U.S. Ser. No. 70,367, filed Aug. 28, 1979, now abandoned.

This invention relates to a method of treating hypertension which comprises administering to a hypertensive subject requiring such treatment, nicotine or a pharmacologically acceptable acid addition salt of nicotine, for an extended period of time.

Nicotine or nicotine related substances have previously been employed or proposed for employment as a treatment for colic (U.S. Pat. No. 101,145), tobacco substitute (U.S. Pat. Nos. 904,521 and 2,981,641), insecticide and parasiticide (U.S. Pat. No. 2,175,980), snake repellent (U.S. Pat. No. 3,069,314), antihistamine potentiator (U.S. Pat. No. 3,126,319), swine food additive (U.S. Pat. No. 3,252,802) and skin care agent (U.S. Pat. No. 2,437,561).

U.S. Pat. No. 3,870,794 discloses administering nicotine and related substances to ameliorate emotional disorders, such as anger, hostility, irritability and frustration.

U.S. Pat. No. 3,048,520 and its French counterpart Brevet Special De Medicament No. 2428M disclose that (-)-cotinine reduces the physiological effects of nicotine. When (-)-cotinine is administered in doses of from 150 to 300 mg, it provides a short term lowering of blood pressure and also is effective as a muscle relaxant. It is stated that "The pressor response to nicotine, i.e. the increase in blood pressure following the administration of nicotine, was blocked by pre-treatment with cotinine."

The effects of administration of nicotine on blood pressure, as applied to various kinds of test animals and using various modes of administration and various amounts of nicotine for various periods of time, have been reported in the literature. A summary of these reports is found in Sections 340 to 349 of "Tobacco-Experimental and Clinical Studies", Supplement III, The Williams & Wilkins Company, Baltimore (1975). The prior research workers have reported achieving both pressor responses and depressor responses, by administration of nicotine, depending on the particular conditions of their experiments. Wenzel and Azmeh (Archives internationales de Pharmacodynamie et de Therapie, Vol. 187, No. 2, pp. 367-376, October 1970) report that chronic administration of nicotine in the drinking water of rats in amounts of 1.14 and 2.28 mg/kg/day produced a gradual elevation of the systolic pressure over a period of 10 weeks, whereas administration of 3.42 mg/kg/day and 4.56 mg/kg/day of nicotine produced lowering of the pressure.

We have discovered that chronic administration of low doses of nicotine or pharmacologically acceptable acid addition salts of nicotine is effective to achieve significant reduction of the diastolic and systolic blood pressures of test subjects that initially have elevated blood pressures, particularly test subjects demonstrating mild and moderate essential hypertension. But such administration does not similarly reduce the blood pressures of test subjects that initially have normal blood pressures.

The antihypertensive effects of nicotine and pharmacologically acceptable acid addition salts of nicotine were experimentally determined as follows:

Nicotine tartrate (0.002-5.0 mg.kg per day) was added to the home cage drinking water of albino rat and squirrel monkey test subjects for periods of from 1 to 10 weeks. The rats received the drug for approximately 8 weeks. Each was then implanted with a chronic aortic cannula, allowed to recuperate, and the blood pressure was measured before and following exposure to a mild tail pinch procedure. All subjects receiving nicotine showed lower blood pressure elevation to noxious stimulation as compared to control subjects which received pure water, and these reductions were greater at higher drug doses. Squirrel monkeys were studied for the effects of ingestion of several chronic nicotine dosages upon resting diastolic and systolic blood pressures. The test subjects differed according to several historical and contemporary factors, with the blood pressures being highest for test subjects with the longest number of years of colony living, months of exposure to noxious stimulation, and elevated body weight. Nicotine administration also caused differing effects in different subjects with differing blood pressure levels. Subjects having high blood pressures showed dose-dependent decreases in blood pressures, whereas subjects possessing low resting pressures demonstrated little or no change during drug intake. A follow-up study with high blood pressure subjects measured the effects of progressive increases in the drug, followed by a return to drug-free water drinking solutions. Here again a dose-dependent decrease in both systolic and diastolic blood pressures was observed. Upon termination of drug intake, pressures rapidly increased to pre-drug levels.

Figure 1:
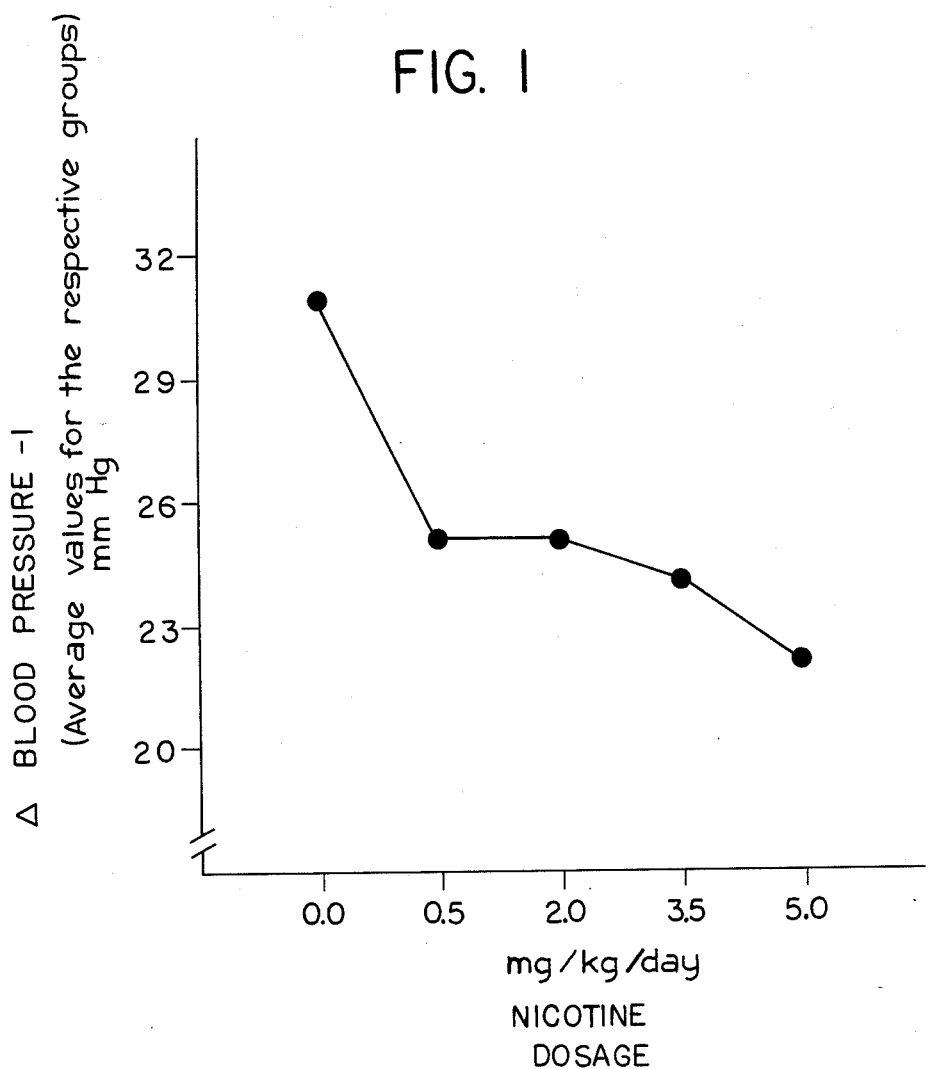
FIG. 1 is a graph showing the change of the blood pressure ($\Delta$ Blood Pressure) caused by a tail pinch as applied to 5 groups of rats respectively receiving distilled water (0.0) or various dosages of nicotine. The blood pressure measured was the hydraulically damped systolic/diastolic average value. The average resting pressures before the tail pinch were (1) 128 mmHg for the group to which was administered 0.0 nicotine, (2) 120 mmHg for the group to which was administered 0.5 mg/kg nicotine, (3) 125 mmHg for the group to which was administered 2.0 mg/kg nicotine, (4) 131 mmHg for the group to which was administered 3.5 mg/kg nicotine and (5) 119 mmHg for the group to which was administered 5.0 mg/kg nicotine.

The FIG. 1 experiment measured the effects of nicotine intake on normotensive subjects during brief stressful episodes. The test subjects were 30 male albino Sprague-Dawley rats weighing 300-400 grams. The subjects were housed individually with free access to food and fluids. The subjects were divided into 5 groups and maintained in the home cages for 11-12 weeks such that each received either distilled water or distilled water containing one of several concentrations of nicotine to assure a nicotine ingestion of 0.5, 2.0, 3.5 or 5.0 mg/kg/day. Forty-eight hours prior to testing each subject was implanted with an aortic cannula. During testing a subject was placed in a small plexiglas cylinder, it's tail was placed between the surfaces of an electromechanically operated clamp device, and secured with adhesive tape to a restraint pole. The clamp device was calibrated to deliver a lateral compression of a force of 150 grams for 1 second upon a 1 inch surface of the tail. Blood pressure and heart rate were obtained by connection of the subject's catheter to a Stratham P23DC pressure transducer and Grass polygraph assembly. The experimental session duration was 30 minutes. Basal pressure recording and equipment calibration required ten minutes. Following this, three tail pinch events occurred at five minute intervals. Five minutes following the third tail pinch a second equipment calibration series was conducted.

The results are shown in FIG. 1. Administration of nicotine caused reduction in the blood pressure increases (Δ Blood Pressure) resulting from the tail pinches. The anti-pressor effect was greater at higher drug levels, and these effects were observed even though no systematic changes in resting blood pressures were observed.

This experiment demonstrated that extended nicotine ingestion produces a decrease in the momentary elevation of blood pressure caused by the brief occurrence of an observable noxious stimulus.

We next studied the effects of nicotine on the resting blood pressures of a colony of squirrel monkeys possessing different life histories and varying blood pressure levels, such that the test animals exhibited mild essential hypertension characteristics to varying degrees.

The test subjects were 30 squirrel monkeys of the laboratory colony (26 males, 4 females) weighing between 500 and 1200 grams. The test subjects were of various ages and had varying histories of exposure to prior experiments. They were housed individually with free access to food and fluids in home cages. Calibrated drink fluid reservoirs on the home cages permitted fluid consumption to be recorded every 24 hours. Following administration of distilled water for a control period of 2 weeks, nicotine tartrate was added to the drinking water so that each subject received 0.002, 0.005, or 0.01 mg/kg/day. Each drug concentration was available in the fluid for a two week period and then was altered to the next higher dosage level. The drug levels were adjusted by adjusting each week the ratio of fresh distilled water and a nicotine-water concentrate, according to the body weight and average daily fluid consumption obtained during that week. The actual drug doses received on a mg/kg/day basis were subsequently computed to be, in all cases, within plus or minus 10%.

The blood pressures were recorded at biweekly intervals. The subjects were lightly anaesthetized with an intraperitoneal dose of 15 mg/kg sodium pentobarbital. Pressures were recorded from the right forearm of the prone subject by use of a sensor (newborn infant) cuff placed over the lower arm inflated to a pressure of 36 mmHg. The output of this cuff was taken through a Statham P23AC transducer to a Grass model 5 polygraph. An occlusion cuff, located proximal to the sensor over the upper arm was manually operated. The test subjects were rank ordered according to their pre-drug diastolic blood pressure and they were treated for purposes of data presentation as 4 groups according to this measure.

The thirty subjects possessed widely differing laboratory histories and physical characteristics. Table 1 presents the average values of the years of residence in the colony, the months of experimental testing, and the body weight, for each group. Experimental testing had in all cases involved daily exposure to noxious stimulation. The blood pressure variations between individual subjects are positively related to each of these conditions.

TABLE 1

Figure 2:
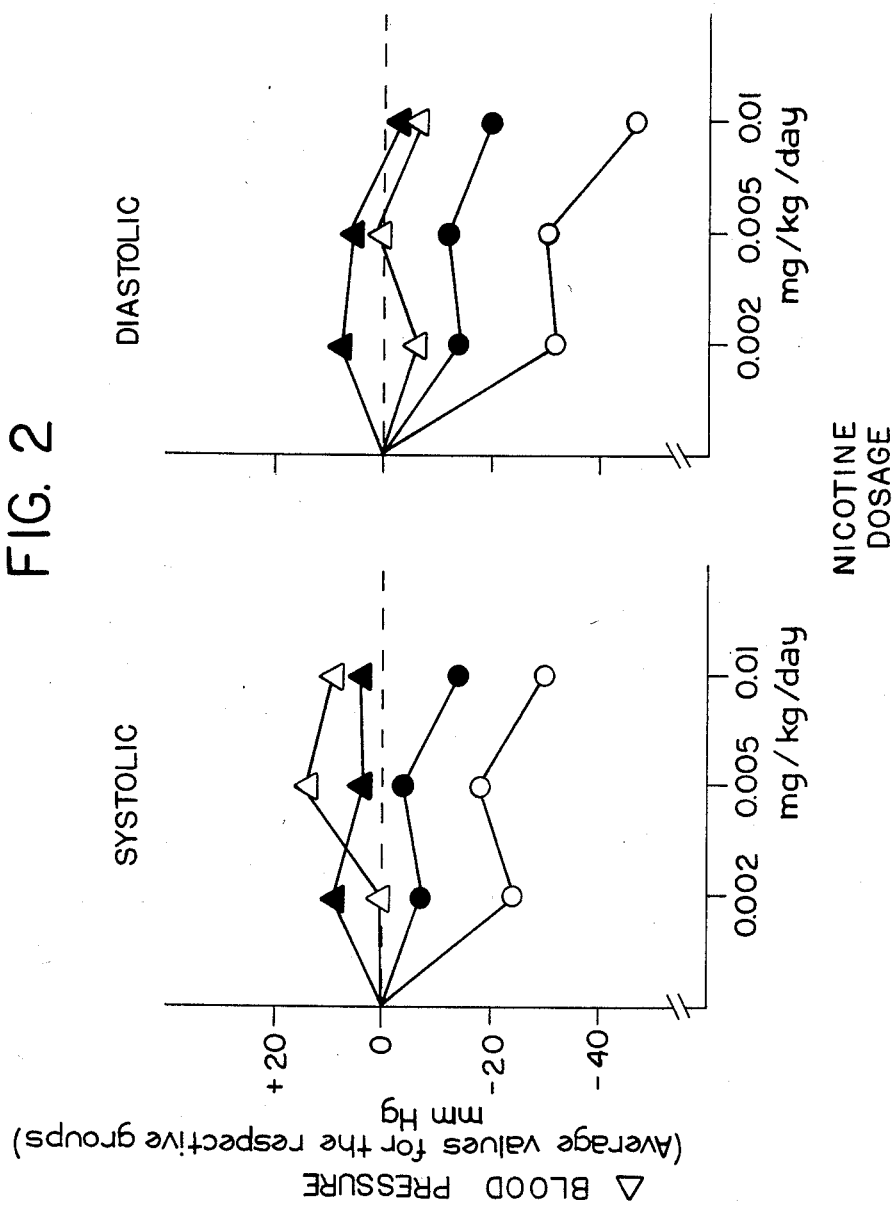
FIG. 2 is a graph showing the change of blood pressure of 30 squirrel monkeys for a chronic drug regimen. The dotted line represents the blood pressure prior to administration of the drug. The open circles represent seven subjects having the highest diastolic blood pressures; the solid circles represent eight subjects having the second highest diastolic blood pressures; the open triangles represent eight subjects having the third highest diastolic blood pressures; and the solid triangles represent seven subjects having the lowest diastolic blood pressures. The blood pressures were measured from the arm of anaesthetized prone subjects.

| Characteristics and Histories of Subjects in Experiment of FIG. 2 | | | | | |
|---|---|---|---|---|---|
| Group | Average pre-drug systolic pressure (mmHg) | Average pre-drug diastolic pressure (mmHg) | Average duration of colony captivity (years) | Average duration of noxious stimulation (months) | Average weight (grams) |
| 1 (seven subjects test mark "O") | 149 | 110 | 6.7 | 17.7 | 888 |
| 2 (eight subjects test mark "●") | 120 | 84 | 6.25 | 9.6 | 894 |
| 3 (eight subjects test mark "▲") | 119 | 77 | 5.19 | 9.25 | 834 |
| 4 (seven subjects test mark "Δ") | 89 | 57 | 4.9 | 10.4 | 785 |

Extended nicotine ingestion produced marked dosedependent decreases in both diastolic and systolic blood pressures in the test subjects ("O" and "●") with elevated pressures and these effects were greatest for subjects with the highest pressures. The pressures of low blood pressure subjects ("▲" and "Δ") were not reduced. Rather, for these subjects, the pressures either remained unchanged or were elevated slightly. FIG. 2 illustrates these effects. During nicotine ingestion the blood pressures for all the groups converged toward similar pressure values. Body weight decreases of 3-5 percent occurred in all subjects during the drug ingestion period. These findings demonstrate that extended nicotine ingestion produces a selective decrease in blood pressure in primate subjects that have chronically elevated pressures, that these pressure reductions are maintained for extended periods, and that the effects are a direct function of dose level and/or duration of drug ingestion.

Figure 3:
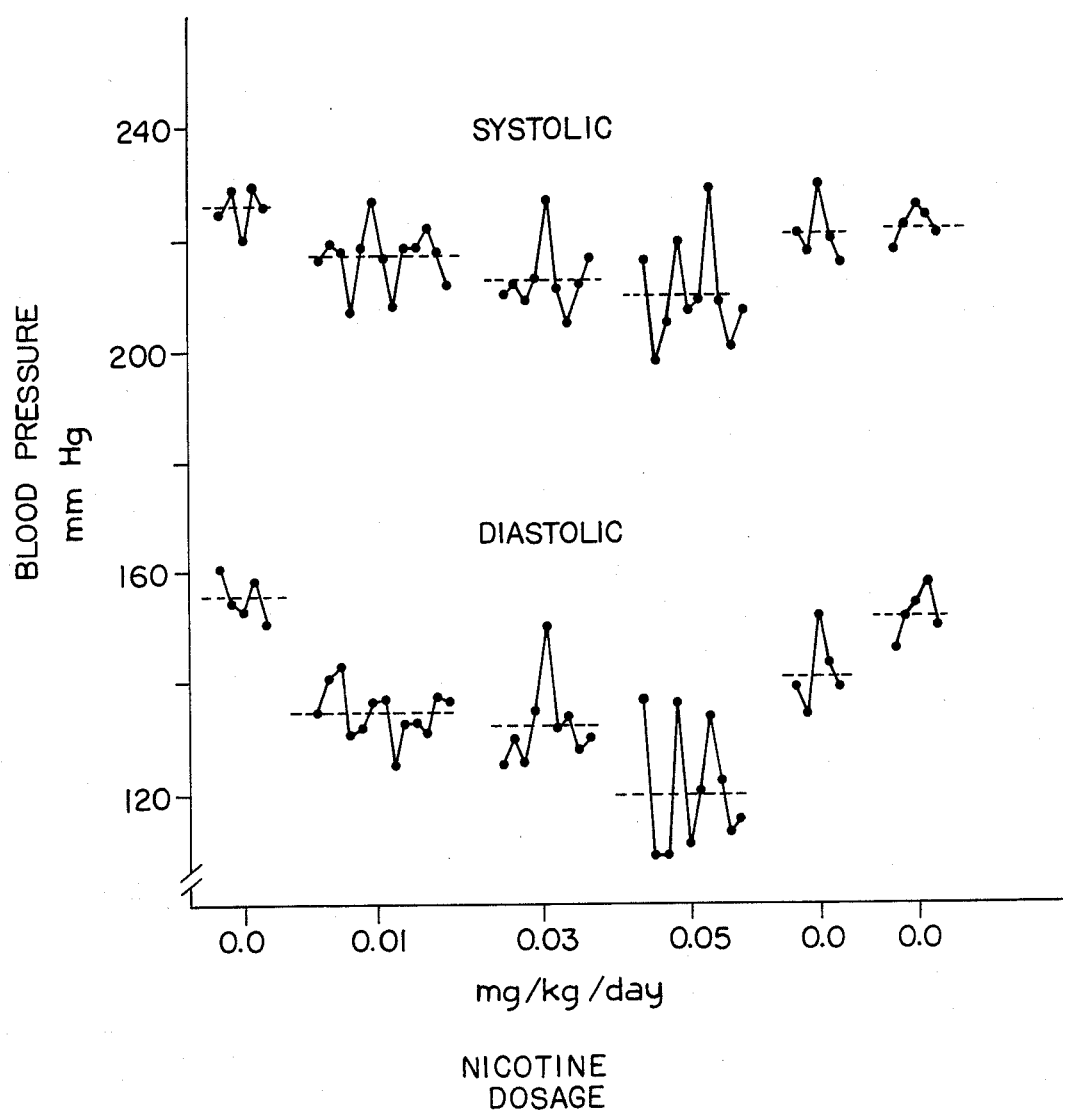
FIG. 3 is a graph showing the average blood pressure readings of 5 squirrel monkeys during a regimen of chronic nicotine administration. The dashed lines are the mean values for the particular dosage levels. The blood pressures were measured from the lower part of the legs of unanesthetized, partially restrained upright subjects.

To assess more thoroughly the effects of drug dose and drug termination, a smaller group was studied in additional tests where all measurements were obtained from fully conscious subjects. The results of these tests are shown in FIG. 3.

The test subjects were five squirrel monkeys (1 female, 4 males) ranging in weight from 500–1100 grams. Each subject had participated in the experiment of FIG. 2 six months previously and, based on diastolic pressure, had ranked in the upper half of the population, four of the five being from the highest blood pressure group ("0"). Calibrated fluid reservoirs were placed on the home cages and fluid consumption was recorded every 24 hours. After a distilled water control period of two weeks, nicotine was added in increasing concentrations so that each subject received 0.01, 0.03, and 0.05 mg/kg/day. Each drug dose was continued for a period necessary to assure measurement stability. Following drug testing, distilled water was again made available. Blood pressure was recorded daily five days a week. The subjects were restrained at the waist in a primate restraint chair located in a sound attenuated chamber. Blood pressure cuffs were placed on the upper and lower right leg. The air inflation procedure was automated and the experimenter and polygraph were located in an adjoining room. The subject was unanaesthetized and allowed a five minute habituation period before any pressures were measured. Pressure measurements were recorded once a minute for five readings. The data points are daily averages for the group.

Ingestion of nicotine was again observed to produce an immediate and marked decrease in both diastolic and systolic pressures of these high blood pressure subjects. Introduction of higher drug doses caused further immediate reductions. When the drug was withdrawn, blood pressures returned within two weeks to the elevated pre-drug levels. Body weight measures again showed a 3–5 percent decrease throughout the drug phase, but the weights did not then increase during the two week post drug period as blood pressures increased.

These results demonstrate that intake of nicotine can cause the reduction or cessation of chronically elevated blood pressure in a primate species The results further show that the effect is dose-dependent and is reversed upon drug termination. The findings also suggest that these effects are not mediated principally by indirect changes in body weight.

Little consensus presently exists regarding the principle pharmacologic actions of nicotine. A general view is that nicotine has ganglionic stimulant properties; the drug can cause increases in respiration, heart rate, blood pressure, and central nervous system activation. Yet recent reports demonstrate that different physiological systems are effected in apparently opposite ways and that the effects of the drug on each of several systems varies with time since administration, duration of exposure, subject preparation, and species.

The experiment of FIG. 1 demonstrated that prolonged ingestion of low doses of nicotine caused a reduction of episodic blood pressure increases resulting from the occurrence of specific noxious events. But drug ingestion did not produce a general pattern of blood pressure decrease.

In the experiment of FIG. 2, prolonged ingestion of nicotine caused selective reductions of deviant, elevated blood pressures that were correlated with extended histories of confinement, noxious stimulation, and elevated body weight. Nicotine administration did not decrease the blood pressures for other subjects that did not possess these characteristics. In the experiment of FIG. 3, it was demonstrated that for high blood pressure subjects, increased drug dosage caused greater blood pressure decreases while termination of drug exposure resulted in return to pre-drug pressure levels. In both experiments 2 and 3, weight losses were noted across the drug regimen but these losses were equivalent for all subjects independent of pre-drug blood pressure level and did not continue to be correlated upon drug removal.

As will be apparent from the foregoing results, nicotine and pharmaceutically acceptable salts of nicotine have an excellent antihypertensive activity. Nicotine and its pharmacologically acceptable acid addition salts when administered in the dosage amounts specified in this application are not toxic to a normal human adult. The drug is rapidly metabolized by the body to relatively inactive, low toxicity substances and is excreted. Tolerance can develop following repeated usage. These compounds are very effective for the treatment of essential hypertension and related conditions. They act on the central nervous systems and modulate the blood pressure of hypertensive subjects, but they do not cause significant unwanted side effects even when used for a long time.

The amounts of nicotine or pharmaceutically acceptable salts of nicotine are appropriately chosen and adjusted depending on the severity of the hypertension condition to be treated. In general, in the case of administration to adult human beings for the purpose of treating hypertension, nicotine and pharmaceutically acceptable salts of nicotine may be orally administered in an amount of from 0.00001 to 1.0 mg/kg/hr, preferably from 0.00007 to 0.02 mg, per kg of body weight, per hour, calculated as nicotine.

The pharmaceutically acceptable acid addition salts of nicotine include nicotine tartrate, nicotine bitartrate, nicotine hydrochloride and nicotine sulfate.

Nicotine and pharmacologically acceptable salts of nicotine can be formed into pharmaceutically acceptable dosage forms for administration for the treatment of hypertension, according to customary techniques, by incorporating therewith an optional pharmaceutical carrier or excipient.

Various dosage forms for oral, inhalation and parenteral administration of nicotine and pharmacologically acceptable salts of nicotine are described in U.S. Pat. No. 3,870,794, the entire contents of which are incorporated herein by reference.

The dosage of the nicotine compound for treatment depends on the route and frequency of administration: the age, weight and condition of the patient; and the severity of the particular hypertensive condition to be treated. Therapeutically effective dosages appropriate for clinically sufficient results can vary from 0.00001 to 1.0 mg/kg/hr, preferably from 0.00007 to 0.02 mg/kg/hr. In the continuous (chronic) treatment according to the invention, the nicotine compound can be administered in appropriately sized dosages 3 or 4 times a day so as to supply, in total, the indicated amount of compound per day.

The embodiments of the invention in which an exclusive property or privilege is claimed are defined as follows:

1. A method of treating essential hypertension which comprises administering to a hypertensive primate subject afflicted with essential hypertension and requiring such treatment, over a period of at least several weeks, a therapeutically effective amount, for chronic treatment to obtain an antihypertensive effect, of nicotine or pharmacologically acceptable acid addition salt of nicotine, in combination with a pharmacologically acceptable carrier, diluent or vehicle.

2. A method according to claim 1 in which said therapeutically effective amount is in the range of about 0.00007 to 0.02 mg per kg of body weight, per hour, calculated as nicotine per hour.

3. A method according to claim 1, in which said salt is selected from the group consisting of nicotine tartrate, nicotine bitartrate, nicotine hydrochloride and nicotine sulfate.

4. A method according to claim 1 or claim 2, in which the administration is oral administration.

5. A method according to claim 1, in which said therapeutically effective amount is in the range of from about 0.000.1 to about 1.0 mg per kg of body weight, per hour, calculated as nicotine.

* * * * *

UNITED STATES PATENT AND TRADEMARK OFFICE
CERTIFICATE OF CORRECTION

PATENT NO. : 4 748 181

DATED : May 31, 1988

INVENTOR(S) : Ronald R. Hutchinson et al

It is certified that error appears in the above-identified patent and that said Letters Patent is hereby corrected as shown below:

Column 7, line 7; delete "per hour".

Column 8, line 7; change "0.000.1" to ---0.00001---.

Signed and Sealed this

Seventh Day of February, 1989

Attest:

DONALD J. QUIGG

Attesting Officer  Commissioner of Patents and Trademarks